(12) United States Patent
Tomai et al.

(10) Patent No.: US 6,610,319 B2
(45) Date of Patent: Aug. 26, 2003

(54) IMMUNE RESPONSE MODIFIER COMPOUNDS FOR TREATMENT OF TH2 MEDIATED AND RELATED DISEASES

(75) Inventors: Mark A. Tomai, Oakdale, MN (US); David M. Hammerbeck, Houlton, WI (US); Karl F. Swingle, Oakdale, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 125 days.

(21) Appl. No.: 09/741,271

(22) Filed: Dec. 19, 2000

(65) Prior Publication Data

US 2002/0041887 A1 Apr. 11, 2002

Related U.S. Application Data

(62) Division of application No. 09/528,620, filed on Mar. 20, 2000, now Pat. No. 6,200,592, which is a division of application No. 08/957,192, filed on Oct. 24, 1997, now Pat. No. 6,039,969.

(60) Provisional application No. 60/029,301, filed on Oct. 25, 1996, and provisional application No. 60/045,331, filed on May 1, 1997.

(51) Int. Cl.$^7$ ............................ A61F 13/00; A61K 31/44
(52) U.S. Cl. .................. 424/434; 374/293; 374/292; 544/126; 504/261
(58) Field of Search ................ 424/434; 514/293, 514/292; 544/126; 504/261

(56) References Cited

U.S. PATENT DOCUMENTS

| | | | |
|---|---|---|---|
| 4,689,338 A | 8/1987 | Gerster | 514/293 |
| 4,929,624 A | 5/1990 | Gerster et al. | 514/293 |
| 5,238,944 A | 8/1993 | Wick et al. | 514/293 |
| 5,266,575 A | 11/1993 | Gerster et al. | 514/293 |
| 5,268,376 A | 12/1993 | Gerster | 514/293 |
| 5,346,905 A | 9/1994 | Gerster | 514/293 |
| 5,352,784 A | 10/1994 | Nikolaides et al. | 544/126 |
| 5,389,640 A | 2/1995 | Gerster et al. | 514/293 |
| 5,395,937 A | 3/1995 | Nikolaides et al. | 514/126 |
| 5,482,936 A | 1/1996 | Lindstrom | 514/293 |
| 5,494,916 A | 2/1996 | Lindstrom et al. | 504/261 |
| 5,525,612 A | 6/1996 | Gerster | 514/293 |
| 5,767,097 A | 6/1998 | Tam | 514/43 |
| 5,856,334 A * | 1/1999 | Mochizuki et al. | 514/292 |
| 6,039,969 A * | 3/2000 | Tomai et al. | |

FOREIGN PATENT DOCUMENTS

| | | |
|---|---|---|
| EP | 0 193 329 A | 9/1986 |
| EP | 385630 | 9/1990 |
| EP | 394026 | 10/1990 |
| WO | 93/20847 | 10/1993 |
| WO | 97/26883 | 7/1997 |
| WO | 98/18810 | 5/1998 |
| WO | 99/11275 | 3/1999 |

OTHER PUBLICATIONS

Hammerbeck, et al, "The Imidazoquinolines And Related Compounds As Inhibitors Of Pulmonary Eosinophilia". *American Journal of Respiratory and Critical Care Medicine*, Apr. 1997, vol. 155, No. 4, part 2.

Varner et al: "Effects of Imiquimod on Post–Viral Asthma–Like Syndrome", *J. of Allergy and Clinical Immunology*, vol. 99, No. 1(2), Jan. 1997, p. s127, XP002055521, Abstract 516.

* cited by examiner

*Primary Examiner*—Michael G. Hartley
*Assistant Examiner*—Robert M DeWitty
(74) *Attorney, Agent, or Firm*—Ted K. Ringsred

(57) ABSTRACT

Immune response modifier compounds—imidazoquinoline amines, imidazopyridine amines, 6,7-fused cycloalkylimidazopyridine amines, and 1,2-bridged imidazoquinoline amines—are useful for the treatment of TH2 mediated diseases by administering a therapeutically effective amount of such compounds in order to inhibit TH2 immune response, suppress IL-4/IL-5 cytokine induction and eosinophilia, as well as enhance TH1 immune response.

1 Claim, No Drawings

IMMUNE RESPONSE MODIFIER COMPOUNDS FOR TREATMENT OF TH2 MEDIATED AND RELATED DISEASES

This application is a divisional of U.S. application Ser. No. 09/528,620, filed March 20, 2000, now U.S. Pat. No. 6,200,592, which is a divisional of Ser. No. 08/957,192, filed Oct. 24, 1997, now U.S. Pat. No. 6,039,969, which claims priority to prior filed provisional applications No. 60/029,301, filed Oct. 25, 1996, and No. 60/045,331, filed May 1, 1997.

BACKGROUND OF THE INVENTION

The present invention relates to the use of immunomodifying imidazoquinoline amines, imidazopyridine amines, 6,7-fused cycloalkylimidazopyridine amines, and 1,2-bridged imidazoquinoline amines to inhibit T helper-type 2 (TH2) immune response and thereby treat TH2 mediated diseases. It also relates to the ability of these compounds to inhibit induction of interleukin (IL)-4 and IL-5, and to suppress eosinophilia.

Many imidazoquinoline amine, imidazopyridine amine, 6,7-fused cycloalkylimidazopyridine amine, and 1,2-bridged imidazoquinoline amine compounds have demonstrated potent immunostimulating, antiviral and antitumor (including anticancer) activity, and have also been shown to be useful as vaccine adjuvants to enhance protective immune system response to vaccines. These compounds are hereinafter sometimes collectively referred to as the "IRM" (immune response modifier) compounds of the invention. Such compounds are disclosed in, for example, U.S. Pat. Nos. 4,689,338, 5,389,640, 5,268,376, 4,929,624, 5,266,575, 5,352,784, 5,494,916, 5,482,936, 5,346,905, 5,395,937, 5,238,944, and 5,525,612, WO 93/20847, and European Patent Application 90,301776,3, wherein their immunostimulating, antiviral and antitumor activities are discussed in detail, and certain specific diseases are identified as being susceptible to treatment therewith, including basal cell carcinoma, eczema, essential thrombocythaemia, hepatitis B, multiple sclerosis, neoplastic diseases, psoriasis, rheumatoid arthritis, type I herpes simplex, type II herpes simplex, and warts. One of these IRM compounds, known as imiquimod, has been commercialized in a topical formulation, Aldara™, for the treatment of anogenital warts associated with human papilloma virus.

The mechanism for the antiviral and antitumor activity of these IRM compounds is thought to be due in substantial part to enhancement of the immune response due to induction of various important cytokines (e.g., interferons, interleukins, tumor necrosis factor, etc.). Such compounds have been shown to stimulate a rapid release of certain monocyte/macrophage-derived cytokines and are also capable of stimulating B cells to secrete antibodies which play an important role in these IRM compounds' antiviral and antitumor activities. One of the predominant immunostimulating responses to these compounds is the induction of interferon (IFN)-α production, which is believed to be very important in the acute antiviral and antitumor activities seen. Moreover, up regulation of other cytokines such as, for example, tumor necrosis factor (TNF), IL-1 and IL-6 also have potentially beneficial activities and are believed to contribute to the antiviral and antitumor properties of these compounds.

However, there are many diseases where the immune system itself actually appears to play a significant role in mediating the disease (i.e., the immune system action takes part in actually causing the disease or an inappropriate type of immune response prevents the correct response from irradicating the disease). Many such diseases are thought to involve a pathologic or inappropriate immune response by the humoral branch of the immune system, which is associated with TH2 cell activity (as opposed to TH1 cell mediated immunity).

The humoral/TH2 branch of the immune system is generally directed at protecting against extracellular immunogens such as bacteria and parasites through the production of antibodies by B cells; whereas the cellular/TH1 branch is generally directed at intracellular immunogens such as viruses and cancers through the activity of natural killer cells, cytotoxic T lymphocytes and activated macrophages. TH2 cells are believed to produce the cytokines IL-3, IL-4, IL-5, and IL-10, which are thought to stimulate production of IgE antibodies, as well as be involved with recruitment, proliferation, differentiation, maintenance and survival of eosinophils (i.e., leukocytes that accept an eosin stain), which can result in eosinophilia. Eosinophilia is a hallmark of many TH2 mediated diseases, such as asthma, allergy, and atopic dermatitis.

The interplay and importance of various aspects of immune system response, including interaction between TH1 and TH2 cell cytokines is discussed in WO 97/2688. Although WO 97/2688 is specifically concerned with the effects of a particular antiviral compound known as Ribavirin®, which is dissimilar to the IRM compounds of the present invention, it nonetheless illustrates some of the complex and unpredictable effects of drug compounds on the immune system.

SUMMARY OF THE INVENTION

It has now been found that in addition to their immunostimulatory, antiviral/antitumor effect on the immune system, the IRM compounds of the present invention—imidazoquinoline amines, imidazopyridine amines, 6,7-fused cycloalkylimidazopyridine amines, and 1,2-bridged imidazoquinoline amines—are also extremely useful for down regulating certain key aspects of the immune response. Specifically, the IRM compounds of the present invention have been found to and inhibit TH2 immune response (in addition to enhancing TH1 immune response). This is extremely important for treating TH2 mediated diseases where an inappropriate TH2 response is causing the disease or preventing eradication of the disease by TH1 response. Thus, when administered in a therapeutically effective amount these IRM compounds can be used for treating TH2 mediated diseases.

An apparently related effect of the present IRM compounds is to inhibit the induction of IL-4, IL-5, and perhaps other cytokines, which thereby allows for treatment of diseases associated with these cytokines. A further important and surprising effect of these compounds is the suppression of eosinophils, which allows for treatment of eosinophilia and related diseases.

Some diseases that are thought to be caused/mediated in substantial part by TH2 immune response, IL-4/IL-5 cytokine induction, and/or eosinophilia (and accordingly responsive to treatment by administering a therapeutically effective amount of the present IRM compounds) include asthma, allergic rhinitis, systemic lupus erythematosis, Ommen's syndrome (hypereosinophilia syndrome), certain parasitic infections, for example, cutaneous and systemic leishmaniasis, toxoplasma infection and trypanosome infection, and certain fungal infections, for example candidiasis and histoplasmosis, and certain intracellular bacterial infections, such as leprosy and tuberculosis. These are examples of non-viral and non-tumor, TH2 mediated diseases for which effective treatment with the present IRM compounds clearly could not have been predicted. Additionally, it should also be noted that diseases having a viral or cancer related basis, but with a significant TH2 mediated pathology can also be beneficially treated with the IRM compounds of the present invention. Particularly preferred uses of the IRM compounds of the present invention are for the treatment of diseases associated with eosinophilia, such as asthma and allergic rhinitis.

The present IRM compounds may be administered via any suitable means, for example, parenterally, transdermally, and orally. One preferred delivery route is via a topical gel or cream formulation. For treatment of asthma and allergic rhinitis, it is preferred to deliver the IRM compound via oral and/or nasal inhalation from a metered dose inhaler.

Particularly preferred IRM compounds include 4-amino-2-ethoxymethyl-α,α-dimethyl-1H-imidazo[4,5-c]quinoline-1-ethanol and 1-(2-methylpropyl)-1H-imidazo[4,5-c]quinolin-4-amine (known as Imiquimod).

Finally, it should be noted that the diseases identified as being treatable in the published patents referred to above in the background (U.S. Pat. Nos. 4,689,338, 5,389,640, 5,268, 376, 4,929,624, 5,266,575, 5,352,784, 5,494,916, 5,482,936, 5,346,905, 5,395,937, 5,238,944, and 5,525,612, WO 93/20847, and European Patent Application 90,301776,3) are generally either viral/tumor based or, if not, are thought not to be TH2 mediated diseases. One exception is eczema, which, although a TH2 mediated disease, is believed to have been identified due to a susceptibility to treatment with interferon (which was then understood to be the main cytokine response induced by the present compounds). There was, however, no recognition at the time that any TH2, IL-4/5, or eosinophilia suppressing ability of the present IRM compounds could be used for treating eczema.

DETAILED DESCRIPTION

Preferred IRM Compounds

As noted above, many of the imidazoquinoline amine, imidazopyridine amine, 6,7-fused cycloalkylimidazopyridine amine, and 1,2-bridged imidazoquinoline amine IRM compounds of the present invention have demonstrated significant immunomodulating activity. Preferred immune response modifier compounds include 1H-imidazo[4,5-c]quinolin-4-amines defined by one of Formulas I-V below:

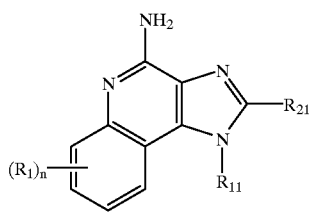

I wherein
$R_{11}$ is selected from the group consisting of alkyl of one to about ten carbon atoms, hydroxyalkyl of one to about six carbon atoms, acyloxyalkyl wherein the acyloxy moiety is alkanoyloxy of two to about four carbon atoms or benzoyloxy, and the alkyl moiety contains one to about six carbon atoms, benzyl, (phenyl)ethyl and phenyl, said benzyl, (phenyl)ethyl or phenyl substituent being optionally substituted on the benzene ring by one or two moieties independently selected from the group consisting of alkyl of one to about four carbon atoms, alkoxy of one to about four carbon atoms and halogen, with the proviso that if said benzene ring is substituted by two of said moieties, then said moieties together contain no more than six carbon atoms;

$R_{21}$ is selected from the group consisting of hydrogen, alkyl of one to about eight carbon atoms, benzyl, (phenyl)ethyl and phenyl, the benzyl, (phenyl)ethyl or phenyl substituent being optionally substituted on the benzene ring by one or two moieties independently selected from the group consisting of alkyl of one to about four carbon atoms, alkoxy of one to about four carbon atoms and halogen, with the proviso that when the benzene ring is substituted by two of said moieties, then the moieties together contain no more than six carbon atoms; and each $R_1$ is independently selected from the group consisting of alkoxy of one to about four carbon atoms, halogen, and alkyl of one to about four carbon atoms, and n is an integer from 0 to 2, with the proviso that if n is 2, then said $R_1$ groups together contain no more than six carbon atoms;

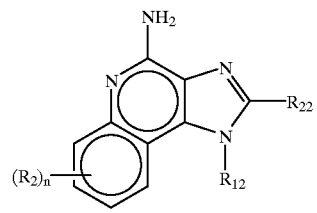

II wherein
$R_{12}$ is selected from the group consisting of straight chain or branched chain alkenyl containing two to about ten carbon atoms and substituted straight chain or branched chain alkenyl containing two to about ten carbon atoms, wherein the substituent is selected from the group consisting of straight chain or branched chain alkyl containing one to about four carbon atoms and cycloalkyl containing three to about six carbon atoms; and cycloalkyl containing three to about six carbon atoms substituted by straight chain or branched chain alkyl containing one to about four carbon atoms; and $R_{22}$ is selected from the group consisting of hydrogen, straight chain or branched chain alkyl containing one to about eight carbon atoms, benzyl, (phenyl)ethyl and phenyl, the benzyl, (phenyl)ethyl or phenyl substituent being optionally substituted on the benzene ring by one or two moieties independently selected from the group consisting of straight chain or branched chain alkyl containing one to about four carbon atoms, straight chain or branched chain alkoxy containing one to about four carbon atoms, and halogen, with the proviso that when the benzene ring is substituted by two such moieties, then the moieties together contain no more than six carbon atoms; and each $R_2$ is independently selected from the group consisting of straight chain or branched chain alkoxy containing one to about four carbon atoms, halogen, and straight chain or branched chain alkyl containing one to about four carbon atoms, and n is an integer from zero to 2, with the proviso that if n is 2, then said $R_2$ groups together contain no more than six carbon atoms;

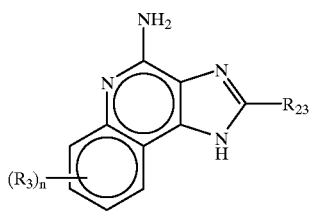

III wherein
- $R_{23}$ is selected from the group consisting of hydrogen, straight chain or branched chain alkyl of one to about eight carbon atoms, benzyl, (phenyl)ethyl and phenyl, the benzyl, (phenyl)ethyl or phenyl substituent being optionally substituted on the benzene ring by one or two moieties independently selected from the group consisting of straight chain or branched chain alkyl of one to about four carbon atoms, straight chain or branched chain alkoxy of one to about four carbon atoms, and halogen, with the proviso that when the benzene ring is substituted by two such moieties, then the moieties together contain no more than six carbon atoms; and
- each $R_3$ is independently selected from the group consisting of straight chain or branched chain alkoxy of one to about four carbon atoms, halogen, and straight chain or branched chain alkyl of one to about four carbon atoms, and n is an integer from zero to 2, with the proviso that if n is 2, then said $R_3$ groups together contain no more than six carbon atoms;

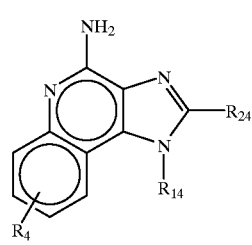

IV wherein
- $R_{14}$ is —$CHR_xR_y$ wherein $R_y$ is hydrogen or a carbon—carbon bond, with the proviso that when $R_y$ is hydrogen $R_x$ is alkoxy of one to about four carbon atoms, hydroxyalkoxy of one to about four carbon atoms, 1-alkynyl of two to about ten carbon atoms, tetrahydropyranyl, alkoxyalkyl wherein the alkoxy moiety contains one to about four carbon atoms and the alkyl moiety contains one to about four carbon atoms, 2-, 3-, or 4-pyridyl, and with the further proviso that when $R_y$ is a carbon—carbon bond $R_y$ and $R_x$ together form a tetrahydrofuranyl group optionally substituted with one or more substituents independently selected from the group consisting of hydroxy and hydroxyalkyl of one to about four carbon atoms;
- $R_{24}$ is selected from the group consisting of hydrogen, alkyl of one to about four carbon atoms, phenyl, and substituted phenyl wherein the substituent is selected from the group consisting of alkyl of one to about four carbon atoms, alkoxy of one to about four carbon atoms, and halogen; and
- $R_4$ is selected from the group consisting of hydrogen, straight chain or branched chain alkoxy containing one to about four carbon atoms, halogen, and straight chain or branched chain alkyl containing one to about four carbon atoms;

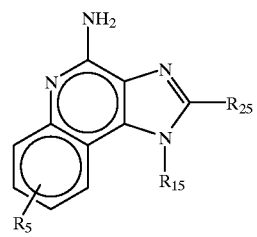

V wherein
- $R_{15}$ is selected from the group consisting of: hydrogen; straight chain or branched chain alkyl containing one to about ten carbon atoms and substituted straight chain or branched chain alkyl containing one to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; straight chain or branched chain alkenyl containing two to about ten carbon atoms and substituted straight chain or branched chain alkenyl containing two to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; hydroxyalkyl of one to about six carbon atoms; alkoxyalkyl wherein the alkoxy moiety contains one to about four carbon atoms and the alkyl moiety contains one to about six carbon atoms; acyloxyalkyl wherein the acyloxy moiety is alkanoyloxy of two to about four carbon atoms or benzoyloxy, and the alkyl moiety contains one to about six carbon atoms; benzyl; (phenyl)ethyl; and phenyl; said benzyl, (phenyl)ethyl or phenyl substituent being optionally substituted on the benzene ring by one or two moieties independently selected from the group consisting of alkyl of one to about four carbon atoms, alkoxy of one to about four carbon atoms, and halogen, with the proviso that when said benzene ring is substituted by two of said moieties, then the moieties together contain no more than six carbon atoms;
- $R_{25}$ is

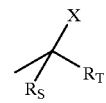

wherein
- $R_S$ and $R_T$ are independently selected from the group consisting of hydrogen, alkyl of one to about four carbon atoms, phenyl, and substituted phenyl wherein the substituent is selected from the group consisting of alkyl of one to about four carbon atoms, alkoxy of one to about four carbon atoms, and halogen;

X is selected from the group consisting of alkoxy containing one to about four carbon atoms, alkoxyalkyl wherein the alkoxy moiety contains one to about four carbon atoms and the alkyl moiety contains one to about four carbon atoms, hydroxyalkyl of one to about four carbon atoms, haloalkyl of one to about four carbon atoms, alkylamido wherein the alkyl group contains one to about four carbon atoms, amino, substituted amino wherein the substituent is alkyl or hydroxyalkyl of one to about four carbon atoms, azido, chloro, hydroxy, 1-morpholino, 1-pyrrolidino, alkylthio of one to about four carbon atoms; and $R_5$ is selected from the group consisting of hydrogen, straight chain or branched chain alkoxy containing one to about four carbon atoms, halogen, and straight chain or branched chain alkyl containing one to about four carbon atoms;

or a pharmaceutically acceptable salt of any of the foregoing.

Preferred 6,7 fused cycloalkylimidazopyridine amine IRM compounds are defined by Formula VI below:

VI

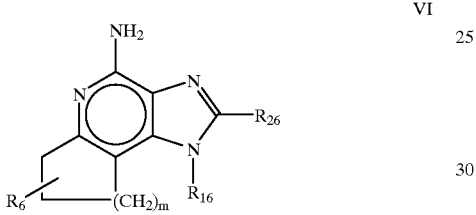

wherein m is 1, 2, or 3;

$R_{16}$ is selected from the group consisting of hydrogen; cyclic alkyl of three, four, or five carbon atoms; straight chain or branched chain alkyl containing one to about ten carbon atoms and substituted straight chain or branched chain alkyl containing one to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; fluoro- or chloroalkyl containing from one to about ten carbon atoms and one or more fluorine or chlorine atoms; straight chain or branched chain alkenyl containing two to about ten carbon atoms and substituted straight chain or branched chain alkenyl containing two to about ten carbon atoms, wherein the substituent is selected from the group consisting of cycloalkyl containing three to about six carbon atoms and cycloalkyl containing three to about six carbon atoms substituted by straight chain or branched chain alkyl containing one to about four carbon atoms; hydroxyalkyl of one to about six carbon atoms; alkoxyalkyl wherein the alkoxy moiety contains one to about four carbon atoms and the alkyl moiety contains one to about six carbon atoms; acyloxyalkyl wherein the acyloxy moiety is alkanoyloxy of two to about four carbon atoms or benzoyloxy, and the alkyl moiety contains one to about six carbon atoms, with the proviso that any such alkyl, substituted alkyl, alkenyl, substituted alkenyl, hydroxyalkyl, alkoxyalkyl, or acyloxyalkyl group does not have a fully carbon substituted carbon atom bonded directly to the nitrogen atom; benzyl; (phenyl)ethyl; and phenyl; said benzyl, (phenyl)ethyl or phenyl substituent being optionally substituted on the benzene ring by one or two moieties independently selected from the group consisting of alkyl of one to about four carbon atoms, alkoxy of one to about four carbon atoms, and halogen, with the proviso that when said benzene ring is substituted by two of said moieties, then the moieties together contain no more than six carbon atoms; and

wherein $R_y$ is hydrogen or a carbon—carbon bond, with the proviso that when $R_y$ is hydrogen $R_x$ is alkoxy of one to about four carbon atoms, hydroxyalkoxy of one to about four carbon atoms, 1-alkynyl of two to about ten carbon atoms, tetrahydropyranyl, alkoxyalkyl wherein the alkoxy moiety contains one to about four carbon atoms and the alkyl moiety contains one to about four carbon atoms, 2-, 3-, or 4-pyridyl, and with the further proviso that when $R_y$ is a carbon—carbon bond $R_y$ and $R_x$ together form a tetrahydrofuranyl group optionally substituted with one or more substituents independently selected from the group consisting of hydroxy and hydroxyalkyl of one to about four carbon atoms, $R_{26}$ is selected from the group consisting of hydrogen, straight chain or branched chain alkyl containing one to about eight carbon atoms, straight chain or branched chain hydroxyalkyl containing one to about six carbon atoms, morpholinomethyl, benzyl, (phenyl)ethyl and phenyl, the benzyl, (phenyl)ethyl or phenyl substituent being optionally substituted on the benzene ring by a moiety selected from the group consisting of methyl, methoxy, and halogen; and —C($R_S$)($R_T$)(X) wherein $R_S$ and $R_T$ are independently selected from the group consisting of hydrogen, alkyl of one to about four carbon atoms, phenyl, and substituted phenyl wherein the substituent is selected from the group consisting of alkyl of one to about four carbon atoms, alkoxy of one to about four carbon atoms, and halogen;

X is selected from the group consisting of alkoxy containing one to about four carbon atoms, alkoxyalkyl wherein the alkoxy moiety contains one to about four carbon atoms and the alkyl moiety contains one to about four carbon atoms, haloalkyl of one to about four carbon atoms, alkylamido wherein the alkyl group contains one to about four carbon atoms, amino, substituted amino wherein the substituent is alkyl or hydroxyalkyl of one to about four carbon atoms, azido, alkylthio of one to about four carbon atoms, and morpholinoalkyl wherein the alkyl moiety contains one to about four carbon atoms, and $R_6$ is selected from the group consisting of hydrogen, fluoro, chloro, straight chain or branched chain alkyl containing one to about four carbon atoms, and straight chain or branched chain fluoro- or chloroalkyl containing one to about four carbon atoms and at least one fluorine or chlorine atom;

and pharmaceutically acceptable salts thereof.

Preferred imidazopyridine amine IRM compounds are defined by Formula VII below:

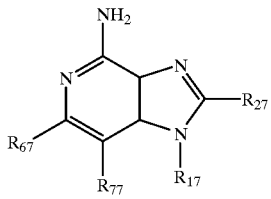

VII wherein
$R_{17}$ is selected from the group consisting of hydrogen; —$CH_2R_W$ wherein $R_W$ is selected from the group consisting of straight chain, branched chain, or cyclic alkyl containing one to about ten carbon atoms, straight chain or branched chain alkenyl containing two to about ten carbon atoms, straight chain or branched chain hydroxyalkyl containing one to about six carbon atoms, alkoxyalkyl wherein the alkoxy moiety contains one to about four carbon atoms and the alkyl moiety contains one to about six carbon atoms, and phenylethyl; and —$CH=CR_ZR_Z$ wherein each $R_Z$ is independently straight chain, branched chain, or cyclic alkyl of one to about six carbon atoms;

$R_{27}$ is selected from the group consisting of hydrogen, straight chain or branched chain alkyl containing one to about eight carbon atoms, straight chain or branched chain hydroxyalkyl containing one to about six carbon atoms, alkoxyalkyl wherein the alkoxy moiety contains one to about four carbon atoms and the alkyl moiety contains one to about six carbon atoms, benzyl, (phenyl)ethyl and phenyl, the benzyl, (phenyl)ethyl or phenyl substituent being optionally substituted on the benzene ring by a moiety selected from the group consisting of methyl, methoxy, and halogen; and morpholinoalkyl wherein the alkyl moiety contains one to about four carbon atoms;

$R_{67}$ and $R_{77}$ are independently selected from the group consisting of hydrogen and alkyl of one to about five carbon atoms, with the proviso that $R_{67}$ and $R_{77}$ taken together contain no more than six carbon atoms, and with the further proviso that when $R_{77}$ is hydrogen then $R_{67}$ is other than hydrogen and $R_{27}$ is other than hydrogen or morpholinoalkyl, and with the further proviso that when $R_{67}$ is hydrogen then $R_{77}$ and $R_{27}$ are other than hydrogen;

and pharmaceutically acceptable salts thereof.

Preferred 1,2-bridged imidazoquinoline amine IRM compounds are defined by Formula VIII below:

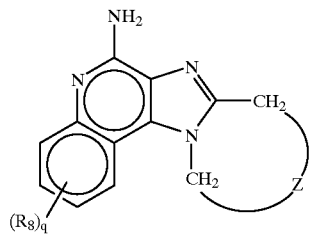

VIII wherein
Z is selected from the group consisting of:

—$(CH_2)_p$— wherein p is 1 to 4;
—$(CH_2)_a$—$C(R_DR_E)(CH_2)_b$—, wherein a and b are integers and a+b is 0 to 3, $R_D$ is hydrogen or alkyl of one to four carbon atoms, and $R_E$ is selected from the group consisting of alkyl of one to four carbon atoms, hydroxy, —$OR_F$ wherein $R_F$ is alkyl of one to four carbon atoms, and —$NR_GR'_G$ wherein $R_G$ and $R'_G$ are independently hydrogen or alkyl of one to four carbon atoms; and
—$(CH_2)_a$—(Y)—$(CH_2)_b$—wherein a and b are integers and a+b is 0 to 3, and Y is O, S, or —$NR_J$— wherein $R_J$ is hydrogen or alkyl of one to four carbon atoms;

and wherein q is 0 or 1 and $R_8$ is selected from the group consisting of alkyl of one to four carbon atoms, alkoxy of one to four carbon atoms, and halogen, and pharmaceutically acceptable salts thereof.

The compounds recited above are disclosed in the patents and applications noted above in the Background.

The substituents $R_{11}$–$R_{17}$ above are generally designated "1-substituents" herein. The preferred 1-substituents are alkyl containing one to six carbon atoms and hydroxyalkyl containing one to six carbon atoms. More preferably the 1-substituent is 2-methylpropyl or 2-hydroxy-2-methylpropyl.

The substituents $R_{21}$–$R_{27}$ above are generally designated "2-substituents" herein. The preferred 2-substituents are hydrogen, alkyl of one to six carbon atoms, alkoxyalkyl wherein the alkoxy moiety contains one to four carbon atoms and the alkyl moiety contains one to four carbon atoms, and hydroxyalkyl of one to four carbon atoms. More preferably the 2-substituent is hydrogen, methyl, butyl, hydroxymethyl, ethoxymethyl or methoxyethyl.

In instances where n can be zero, one, or two, n is preferably zero or one.

The amounts of these IRM compounds that will be therapeutically effective in a specific situation will of course depend on such things as the activity of the particular compound, the mode of administration, and the disease being treated. As such, it is not practical to identify specific administration amounts herein; however, those skilled in the art will be able to determine appropriate therapeutically effective amounts based on the guidance provided herein, information available in the art pertaining to these compounds, and routine testing.

Immune System Mechanisms

Recent evidence indicates that the immune system can be broken down into two major arms, the humoral and cellular arms. The humoral arm is important in eliminating extracellular pathogens such as bacteria and parasites through production of antibodies by B cells. On the other hand, the cellular arm is important in the elimination of intracellular pathogens such as viruses through the activity of natural killer cells, cytotoxic T lymphocytes and activated macrophages. In recent years it has become apparent that these two arms are activated through distinct T helper cell (TH) populations and their distinct cytokine production profiles. T helper type 1 (TH1) cells are believed to enhance the cellular arm of the immune response and produce predominately the cytokines IL-2 and IFN-γ; whereas, T helper 2 (TH2) cells are believed to enhance the humoral arm of the immune response and produce cytokines, such as interleukin-3 (IL-3), interleukin-4 (IL-4), interleukin-5 (IL-5) and granulocyte-macrophage colony-stimulating factor (GM-CSF). In the TH2 case, IL-3, IL-5 and GM-CSF are thought to stimulate eosinophilopoiesis. In addition, IL-5 facilitates terminal differentiation and cell proliferation of eosinophils and promotes survival, viability and migration of eosinophils, while IL-4 stimulates production of antibodies of the IgE class. IgE is an important component in allergies and asthma. IL-5 may also prime eosinophils for the subsequent actions of other mediators.

In contrast, the TH1 cytokines, IL-2 and IFN-γ, are important in activating macrophages, NK cells and CTL (cytotoxic T lymphocytes). IFN-γ also stimulates B cells to secrete specifically cytophilic antibody for the elimination of virally-infected cells. Interestingly, IFN-α, a macrophage-derived cytokine has been shown to antagonize TH2-type responses. IFN-α also appears to inhibit the proliferation and cytokine production of TH2 cells and enhances IFN-γ production by TH1 cells. In addition, IFN-α also appears to inhibit IgE production and antigen-induced increases in IL4 mRNA levels.

TH1 Stimulation Versus TH2 Down Regulation

IRM compounds of the present invention have been shown in a number of models to augment cell mediated immunity, which is consistent with stimulation of TH1 cells. Surprisingly, in models of eosinophilia (TH2/humoral immune mediated process) these compounds actually inhibit the eosinophilia. Further studies indicate that the way in which these compounds are achieving this is in part by their ability to inhibit TH2 cell production of the cytokine IL-5. We have shown in both in vitro and in vivo models, inhibition of IL-5 production by imidazoquinolines. For example, as shown in Table 1, an exemplary IRM compound 4-amino-2-ethoxymethyl-α,α-dimethyl-1H-imidazo[4,5-c]quinoline-1-ethanol dramatically inhibits IL-5 production in spleen cell cultures stimulated with antigen. Spleen cells from OVA-sensitized CFW mice ($2 \times 10^6$/ml) were cultured for 96 hr with OVA (100 μg/ml). Some cultures also received this IRM compound over a range of concentrations. Culture supernatants were collected and analyzed by ELISA (Endogen) for IL-5. Results are presented as the mean of triplicate cultures±SEM. IL-5 concentration is in pg/ml.

TABLE 1

Inhibition of Mouse Spleen Cell Production of IL-5

| Treatment | IRM Compound Concentration | IL-5 Concentration (pg/ml) |
| --- | --- | --- |
| OVA alone |  | 240 ± 20 |
| OVA + IRM Compound | 10 μg/ml | 12 ± 2 |
| OVA + IRM Compound | 1 μg/ml | 22 ± 3 |
| OVA + IRM Compound | 0.1 μg/ml | 25 ± 8 |
| OVA + IRM Compound | 0.01 μg/ml | 125 ± 46 |
| Medium |  | 57 ± 27 |

As can be seen from Table 1, concentrations of IRM compound as low as 0.01 μg/ml inhibit IL-5 production by greater than 60%; whereas, higher concentrations inhibit IL-5 production by 100%.

In vivo, the exemplary IRM compound 4-amino-2-ethoxymethyl-α,α-dimethyl-1H-imidazo[4,5-c]quinoline-1-ethanol was shown to inhibit antigen induced IL-5 production in a dose dependent manner, as shown in Table 2. CFW male mice were sensitized with OVA as described above. 14 days after the last sensitization animals were challenged with 100 μg OVA sc. Some animals received the free-base of 4-amino-2-ethoxymethyl-α,α-dimethyl-1H-imidazo[4,5-c]quinoline-1-ethanol po either at the same time of OVA challenge or 24 hrs before. Serum was collected 7 hrs after OVA and analyzed for IL-5 and IFN-γ concentrations. Results are expressed as the mean cytokine concentration±SEM.

TABLE 2

Effects of IRM Compounds on IL-5 and IFN-γ Production

| IRM Compound | Cytokine Concentration (pg/mL) ± SEM | |
| --- | --- | --- |
| Dose (mg/kg) | −24 hr IL-5 (pg/mL) | 0 hr IL-5 (pg/mL) |
| 0.01 | 78 | 96 |
| 0.1 | 49 | 62 |
| 1.0 | 38 | 40 |
| 10.0 | 8 | 29 |
| Sen. Control | 213 | 270 |
| Normal Control | 1 | 1 |

It can thus be seen that 4-amino-2-ethoxymethyl-α,α-dimethyl-1H-imidazo[4,5-c]quinoline-1-ethanol was active when given either at the same time of antigen challenge or when given a day before antigen. Doses as low as 0.01 mg/kg inhibited IL-5 production by at least 65%.

One common feature of many TH2 mediated diseases is an accumulation of eosinophils, referred to as eosinophilia. For example, chronic pulmonary inflammation involving eosinophil infiltration is a characteristic hallmark feature of bronchial asthma. Increased numbers of eosinophils have been observed in blood, bronchoalveolar lavage fluid and pulmonary tissue in patients with asthma, but the mechanism(s) responsible for their recruitment into and regulation within pulmonary tissues undergoing allergic or pro-inflammatory reactions has not been fully understood. Mediators and cytokines from T-lymphocytes and effector cells such as basophils, mast cells, macrophages and eosinophils have been implicated in enhancing cell maturation, chemotaxis and activation of eosinophils. Evidence suggests that an association exists between the immune system, especially $CD4^+$ T cells, and eosinophils and eosinophil recruitment. Studies in asthmatics and in animal models of allergic pulmonary responses support this notion with the evidence of close correlations between the relative numbers of T cells and activated eosinophils in the airways. The importance of T-lymphocyte in eosinophil recruitment is strengthened by studies with T cell-selective immunosuppressive agents like cyclosporin A, FK506 and cyclophosphamide. These agents have been shown to reduce eosinophilia. Immunostimulants on the other hand have generally not been shown to clearly reduce eosinophilia. However, this may be a reflection on how these immunostimulants are affecting the immune system.

The following three sets of studies clearly indicate that the IRM compounds of the present invention can be used to suppress eosinophilia.

The first set of studies evaluate the IRM compound 4-amino-2-ethoxymethyl-α,α-dimethyl-1H-imidazo[4,5-c]quinoline-1-ethanol for its ability to inhibit antigen-induced eosinophilia in the lung after aerosol challenge with antigen. Results in Table 3 show that 4-amino-2-ethoxymethyl-α,α-dimethyl-1H-imidazo[4,5-c]quinoline-1-ethanol at 1 mg/kg is capable of inhibiting antigen-induced eosinophilia in the lung of mice by 78% when given 15 minutes prior to antigen challenge. Concentrations of IL-4 were reduced in the BAL of these mice by 43% when compared to animals receiving antigen alone. Also, the IRM compound induced inhibition of eosinophilia correlated with a significant inhibition in BAL concentrations of IL-5, which were reduced by 78%. CFW mice were sensitized on day 0 with 10 μg of ovalbumin (OVA) ip in 1% alum and then boosted 7 days later with the same regimen. Fourteen days after boosting animals were dosed by nebulization for 30 minutes using a 1% OVA solution. This was repeated on days 17 and 20. Twenty-four hours after the final nebulized dose animals were sacrificed and bronchoalveolar lavage (BAL) was performed using 1.0 ml of PBS containing 1% fetal bovine serum. BAL was stored at −70° C. before analyzed. Lungs were then removed and placed in 0.5% cetrimide, 0.05 M KH2PO4 for homogenization of 4×30 seconds with 30 second cooling intervals between on ice. Centrifugation was then done at 1300 rpm (400×g) for 30 minutes at 4 C. Pellet was collected and resuspended in 4 ml 0.5% cetrimide, 0.05 M KH2PO4 buffer. Samples were then frozen until sonication and the EPO assessment. This was followed by sonication for 3×15 seconds with 30 second intervals on ice.

An EPO (eosinophil peroxidase, an eosinophil protein used as a marker of eosinophil presence) assay consisted of determining the levels of EPO in the lung tissue (or supernatant of BAL fluid) from each individual guinea pig sample. 50 ul of the "sample solution" consisting of 375 ul PBS (pH 7, RT)+25 ul 0.05 M TRIS-HCL containing 2% Triton (pH 8, RT)+50 ul of sonicated lung lobe was added to 860 ul 0.05 M TRIS-HCL containing 0.1% Triton (pH 8, RT) in combination with 8.5 ul mM 0-phenylenediaminedihydrochloride (OPD). To start the reaction, 1 ul of 30% hydrogen peroxide was added to the cuvette. The optical density reading was measured spectrophotometrically over a 4 minute time interval at 490 nm in a Beckman Du-64 spectrophotometer.

BAL were analyzed by ELISA (Endogen) for IL-5 and IL-4 concentrations with data being presented as the average from 11 animals±SEM. Results are presented as the mean of triplicate cultures±SEM. IL-5 concentration is in pg/ml.

TABLE 3

Inhibition of Antigen-induced Lung Eosinophilia, IL-5 and IL-4

| Treatment | EPO Concentration in Lung (ABS) | IL-5 Concentration in BAL (pg/ml) | IL-4 Concentration in BAL (pg/ml) |
|---|---|---|---|
| Non sensitized Control | 258 ± 28 | 0.8 ± 0.3 | 30 ± 3 |
| Antigen Sensitized | 600 ± 87 (100) | 59 ± 18 (100) | 70 ± 10 (100) |
| IRM Compound + Antigen | 352 ± 30 (78)* | 13 ± 2 (78)* | 53 ± 8 (42) |

* = Significant difference from ovalbumin control group at α = 0.05

The second set of studies evaluated the two IRM compounds 4-amino-α,α-2-trimethyl-1H-imidazo[4,5-c]quinoline-1-ethanol (Cmpd 1) and 4-amino-2-ethoxymethyl-α,α-dimethyl-1H-imidazo[4,5-c]quinoline-1-ethanol (Cmpd 2) for their ability to inhibit sephadex-induced eosinophilia in the lung intravenous sephadex challenge. Results in Table 4 show that oral administration or intratracheal instillation of IRM Cmpd Ex. 1 at ≧0.7 mg/kg and oral administration of Cmpd 2 at ≧0.01 mg/kg are capable of inhibiting sephadex-induced eosinophilia in the lung of rats when given 60 minutes prior to challenge. A maximum inhibition of 95% occurred with Cmpd 1 and 87% occurred with Cmpd 2.

Male, Sprague Dawley rats were injected on day 0 with sephadex G-200 particles in a lateral tail vein (0.5 mg/rat). On days 14–16, the rats were lightly anesthetized with halothane and subsequently dosed with either drug or vehicle (1.0 mg/kg, orally) 24 hours and 1 hour before a second sephadex challenge on day 14. A booster of Sephadex G-200 particles was administered intravenously in a lateral tail vein (0.5 mg/rat) at 1 hour post-drug (i.e., following either drug or vehicle) on day 14 only. The animals are sacrificed on day 17 at 72 hrs. post-sephadex dosing by lethal injection of sodium pentobarbital (100–125 mg/kg, ip). Lungs were exanguinated, lavaged, and removed. They were then placed in 0.5% cetrimide, 0.05 M KH2PO4 for homogenization of 4×30 seconds with 30 second cooling intervals between on ice. Centrifugation was then done at 1300 rpm (400×g) for 30 minutes at 4 C. Pellet was collected and resuspended in 4 ml 0.5% cetrimide, 0.05 M KH2PO4 buffer. Samples were then frozen until sonication and the EPO assessment. This was followed by sonication for 3×15 seconds with 30 second intervals on ice.

The EPO (eosinophil peroxidase, an eosinophil protein used as a marker of eosinophil presence) assay consisted of determining the levels of EPO in the lung tissue (or supernatant of BAL fluid) from each individual rat sample. 50 ul of the "sample solution" consisting of 375 ul PBS (pH 7, RT)+25 ul 0.05 M TRIS-HCL containing 2% Triton (pH 8, RT)+50 ul of sonicated lung lobe was added to 860 ul 0.05 M TRIS-HCL containing 0.1% Triton (pH 8, RT) in combination with 8.5 ul mM 0-phenylenediaminedihydrochloride (OPD). To start the reaction, 1 ul of 30% hydrogen peroxide was added to the cuvette. The optical density reading was measured spectrophotometrically over a 4 minute time interval at 490 nm in a Beckman Du-64 spectrophotometer.

TABLE 4

Inhibition of Sephadex-induced Lung Eosinophilia in Rats

| Treatment | Drug mg/k | EPO Concentration in the Lung[b,c] (X ± SE) | % Inhibition |
|---|---|---|---|
| Group 1: Cmpd 1 Intratracheal Instillation | | | |
| Non-Sephadex Control | 0.0 | 0.0923 ± 0.017 | |
| Sephadex Challenged | 0.0 | 0.5456 ± 0.085 | |
| Drug + Sephadex Challenged | 0.03 | 0.7107 ± 0.129 | 0% |
| | 0.1 | 0.5030 ± 0.089 | 9% |
| | 0.3 | 0.3440 ± 0.201 | 44% |
| | 0.7 | 0.1967 ± 0.080* | 77% |
| Group 2: Cmpd 1 Oral Administration | | | |
| Non-Sephadex Control | 0.0 | 0.0390 ± 0.008 | |
| Sephadex Challenged | 0.0 | 0.3453 ± 0.100 | |
| Drug + Sephadex Challenged | 0.1 | 0.4240 ± 0.138 | 0% |
| | 0.7 | 0.1497 ± 0.030* | 64% |
| | 1.0 | 0.0780 ± 0.039* | 87% |
| | 5.0 | 0.0790 ± 0.030* | 87% |
| | 30.0 | 0.0550 ± 0.013* | 95% |
| Group 3: Cmpd 2 Oral Administration | | | |
| Non-Sephadex Control | 0.0 | 0.1072 ± 0.020 | |
| Sephadex Challenged | 0.0 | 0.6738 ± 0.100 | |
| Drug + Sephadex Challenged | 0.001 | 0.6775 ± 0.140 | 0% |
| | 0.01 | 0.4908 ± 0.070* | 32% |
| | 0.1 | 0.2000 ± 0.060* | 84% |
| | 1.0 | 0.1824 ± 0.060* | 87% |

* = Significant difference from ovalbumin control group at α = 0.05

The third set of studies evaluated 4-amino-α,α-2-trimethyl-1H-imidazo[4,5-c]quinoline-1-ethanol (Cmpd 1) and 4-amino-2-ethoxymethyl-α,α-dimethyl-1H-imidazo[4,5-c]quinoline-1-ethanol (Cmpd 2) for their ability to inhibit ovalbumin-induced eosinophilia in the lung aerosol antigen challenge. Results in Table 5 show that intraperitoneal administration or aerosol inhalation of Cmpd 1 at 0.01 mg/kg and oral administration of Cmpd 2 at 0.01 mg/kg are capable of inhibiting ovalbumin-induced eosinophilia in the lung of guinea pigs when given either 15 or 60 minutes prior to challenge, respectively. A maximum inhibition of 92% occurred with IRM Cmpd 1 and 96% occurred with IRM Cmpd 2. In the guinea pig, these two imidazoquinoline compounds produce approximately equivalent effects on ovalbumin-induced lung eosinophilia.

Male Hartley guinea pigs (~250–500 g), sensitized to ovalbumin (50 mg/kg, ip, greater than or equal to 14 days) were dosed with chlorpheniramine (5 mg/kg, ip) and drug or vehicle intratracheally (or by another route) at 15 minutes pre-challenge. Animals were placed inside an inverted dessicator jar which was placed onto a plexiglass platform. The platform allowed for aerosolization of $H_2O$ or ovalbumin (50 mg/ml) for 5 minutes via a No. 40 DeVilbiss nebulizer, and for providing a constant flow of air into the chamber from a continuous air source. Animals were sacrificed at 24 hrs. post-challenge by lethal injection of sodium pentobarbital (100–125 mg/kg, ip). Lungs were exanguinated, lavaged, and removed. They were then placed in 0.5% cetrimide, 0.05 M KH2PO4 for homogenization of 4×30 seconds with 30 second cooling intervals between on ice. Centrifugation was then done at 1300 rpm (400×g) for 30 minutes at 4 C. Pellet was collected and resuspended in 4 ml 0.5% cetrimide, 0.05 M KH2PO4 buffer. Samples were frozen until assayed. This was followed by sonication for 3×15 seconds with 30 second intervals on ice.

The EPO (eosinophil peroxidase, an eosinophil protein used as a marker of eosinophil presence) assay consisted of determining the levels of EPO in the lung tissue (or supernatant of BAL fluid) from each individual guinea pig sample. 50 ul of the "sample solution" consisting of 375 ul PBS (pH 7, RT)+25 ul 0.05 M TRIS-HCL containing 2% Triton (pH 8, RT)+50 ul of sonicated lung lobe was added to 860 ul 0.05 M TRIS-HCL containing 0.1% Triton (pH 8, RT) in combination with 8.5 ul mM 0-phenylenediaminedihydrochloride (OPD). To start the reaction, 1 ul of 30% hydrogen peroxide was added to the cuvette. The optical density reading was measured spectrophotometrically over a 4 minute time interval at 490 nm in a Beckman Du-64 spectrophotometer.

TABLE 5

Inhibition of Ovalbumin-Induced Lung Eosinophilia in the Guinea Pig

| Treatment | Drug mg/k | EPO Concentration in the Lung$^{b,c}$ (X ± SE) | % Inhibition |
|---|---|---|---|
| Group 1: Cmpd 1 Aerosol Inhalation | | | |
| Non-Ovalbumin Control | 0.0 | 0.0312 ± 0.005 | |
| Ovalbumin Challenged | 0.0 | 0.2959 ± 0.035 | |
| Drug + Ovalbumin Challenged | 0.003 | 0.2620 ± 0.116 | 13% |
| | 0.01 | 0.1806 ± 0.035* | 44% |
| Group 2: Cmpd 1 Intraneritoneal Administration | | | |
| Non-Ovalbumin Control | 0.0 | 0.0338 ± 0.004 | |
| Ovalbumin Challenged | 0.0 | 0.3268 ± 0.046 | |
| Drug + Ovalbumin Challenged | 0.003 | 0.2435 ± 0.0515 | 28% |
| | 0.01 | 0.1690 ± 0.053* | 54% |
| | 0.03 | 0.1693 ± 0.060* | 54% |
| | 3.0 | 0.0580 ± 0.018* | 92% |
| Group 3: Cmpd 2 Oral Administration | | | |
| Non-Ovalbumin Control | 0.0 | 0.0203 ± 0.008 | |

TABLE 5-continued

Inhibition of Ovalbumin-Induced Lung Eosinophilia in the Guinea Pig

| Treatment | Drug mg/k | EPO Concentration in the Lung$^{b,c}$ (X ± SE) | % Inhibition |
|---|---|---|---|
| Ovalbumin Challenged | 0.0 | 0.2307 ± 0.010 | |
| Drug + Ovalbomin Challenged | 0.001 | 0.1862 ± 0.030 | 19% |
| | 0.01 | 0.1181 ± 0.020* | 49% |
| | 0.1 | 0.0118 ± 0.005* | 95% |
| | 1.0 | 0.0084 ± 0.005* | 96% |

* = Significant difference from ovalbumin control group at $\alpha = 0.05$

The above studies indicate that the IRM compounds of the present invention can be used for treatment of TH2 mediated diseases by inhibiting TH2 immune responses, and suppressing IL-4 and IL-5 induction and eosinopilia. Examples of such diseases include asthma, allergy, atopic dermatitis, early HIV disease, infectious mononucleosis, and systemic lupus erythematosis. There is also an association with an increased TH2 response in Hodgkin's and non-Hodgkin's lymphoma as well as embryonal carcinoma. Moreover, the ability of the IRM compounds of the present invention to inhibit TH2 response and augment TH1 response indicates that these compounds will be useful in treating parasitic infections, for example, cutaneous and systemic leishmaniasis, Toxoplasma infection and Trypanosome infection, certain fungal infections, for example Candidiasis and Histoplasmosis, and intracellular bacterial infections, such as leprosy and tuberculosis. Studies in mice infected with leishmania major have shown that a TH1 response correlates with resistance, whereas a TH2 response correlates with susceptibility. Also studies in mice have shown that parasites that live in macrophages, for example, leishmania major, are killed when the host cells are activated by interferon-γ, which is known to be a TH1 cell product. In mice infected with candida and histoplasma, it is known that a TH1 response correlates with resistance, whereas a TH2 response correlates with susceptibility.

Accordingly, from all of the above, it is apparent that the imidazoquinoline amines, imidazopyridine amines, 6,7-fused cycloalkylimidazopyridine amines, and 1,2-bridged imidazoquinoline amines of the present invention are useful for treating TH2 mediated and other related diseases. Although the invention has been presented in terms of preferred embodiments and specific examples, there is no intention to limit the invention to such embodiments and examples. Additionally, it is intended that the disclosures of all the documents referred to in the preceding disclosure are expressly incorporated herein by reference.

We claim:

1. A method of inhibiting induction of IL-4 and/or IL-5 cytokines to treat a non-viral non-tumor disease comprising administering an immune response modifier compound that is an imidazo[4,5-c]quinoline amine, in an amount effective to inhibit said IL-4 and/or IL-5 cytokines, with the proviso that said disease is other than eczema.

* * * * *